US010188571B2

(12) United States Patent
Wyslucha et al.

(10) Patent No.: US 10,188,571 B2
(45) Date of Patent: Jan. 29, 2019

(54) ADAPTER FOR CONNECTING AT LEAST ONE ACCESSORY DEVICE TO AN OPERATING TABLE

(71) Applicant: MAQUET GmbH & CO. KG, Rastatt (DE)

(72) Inventors: Ulrich Wyslucha, Weingarten (DE); Marco Reif, Forbach (DE)

(73) Assignee: MAQUET GMBH & CO. KG, Rastatt (DE)

( * ) Notice: Subject to any disclaimer, the term of this patent is extended or adjusted under 35 U.S.C. 154(b) by 0 days.

(21) Appl. No.: 14/680,923

(22) Filed: Apr. 7, 2015

(65) Prior Publication Data

US 2015/0272803 A1     Oct. 1, 2015

Related U.S. Application Data

(63) Continuation of application No. 12/893,058, filed on Sep. 29, 2010, now Pat. No. 8,997,286.

(30) Foreign Application Priority Data

Sep. 30, 2009   (DE) .................. 10 2009 047 869

(51) Int. Cl.
*A61G 13/10*     (2006.01)
*A61G 13/00*     (2006.01)
(Continued)

(52) U.S. Cl.
CPC ....... *A61G 13/101* (2013.01); *A61G 13/0036* (2013.01); *A61G 13/0081* (2016.11);
(Continued)

(58) Field of Classification Search
CPC ............ A61G 13/101; A61G 13/0036; A61G 13/123; A61G 13/1245; A61G 13/128;
(Continued)

(56) References Cited

U.S. PATENT DOCUMENTS 3,020,909 A * 2/1962 Stevens ............. A61G 13/0036
                                                    5/623
3,046,072 A    7/1962 Douglass et al.
(Continued)

FOREIGN PATENT DOCUMENTS

CN     0326763 A     2/1958
EP      923922 A2    6/1999
WO   2009062324 A1   5/2009

OTHER PUBLICATIONS (Internet accessed article), Matta, Joel M., "*The Anterior Approach for Total Hip Arthroplasty: Background and Operative Technique*", Good Samaritan Hospital, Los Angeles, CA, USA, printed for IDS submission and accessed online on Dec. 12, 2014 at http://www.mizuhosi.com/wp-content/uploads/AA-updated-surg-tech.pdf.
(Continued)

*Primary Examiner* — Eric J Kurilla
*Assistant Examiner* — Amanda L Bailey
(74) *Attorney, Agent, or Firm* — Aaron M. Miller

(57) ABSTRACT

An adapter is described for connecting at least one accessory device to an operating table, comprising a first fixing device for attaching a base body of the adapter to the operating table and a second fixing device for attaching the accessory device to the adapter. The base body is formed from an X-ray transparent plate, said X-ray transparent plate including a part lying on a support surface of the operating table and another part extending beyond the support surface and forming a support surface extension for supporting a patient, when said X-ray transparent plate is attached to the operating table.

19 Claims, 13 Drawing Sheets

(51) Int. Cl.
*A61G 13/12* (2006.01)
*A61B 90/57* (2016.01)

(52) U.S. Cl.
CPC ...... *A61B 2090/571* (2016.02); *A61G 13/123* (2013.01); *A61G 13/1245* (2013.01)

(58) Field of Classification Search
CPC .......... A61G 13/126; A61G 2013/0081; A61G 2013/0072; A61G 2013/0063; A61G 2013/0045; A61B 2090/571
See application file for complete search history.

(56) References Cited

U.S. PATENT DOCUMENTS

| | | | | |
|---|---|---|---|---|
| 3,090,381 | A | * | 5/1963 | Watson .............. A61G 13/0036 5/624 |
| 3,509,876 | A | | 5/1970 | Pilz |
| 3,599,964 | A | | 8/1971 | Magni |
| 3,624,396 | A | * | 11/1971 | Watson ..................... A61F 5/04 378/189 |
| 4,143,652 | A | | 3/1979 | Meier et al. |
| 4,373,709 | A | | 2/1983 | Whitt |
| 4,428,571 | A | | 1/1984 | Sugarman |
| 4,443,005 | A | * | 4/1984 | Sugarman .............. A61G 13/12 378/208 |
| 4,660,817 | A | | 4/1987 | Kowalski |
| 4,872,656 | A | | 10/1989 | Brendgord et al. |
| 4,913,413 | A | * | 4/1990 | Raab ....................... A61G 13/00 269/328 |
| 5,390,383 | A | * | 2/1995 | Carn ..................... A61G 13/12 128/877 |
| 5,528,782 | A | | 6/1996 | Pfeuffer et al. |
| 5,645,079 | A | * | 7/1997 | Zahiri ................... A61F 5/3769 128/882 |
| 5,675,851 | A | * | 10/1997 | Feathers ................ A61G 13/12 108/69 |
| 5,806,117 | A | | 9/1998 | Gotfried |
| 6,012,456 | A | | 1/2000 | Schuerch |
| 6,237,172 | B1 | | 5/2001 | Morgan, Sr. ..................... 5/618 |
| 6,286,164 | B1 | | 9/2001 | Lamb et al. |
| 6,295,671 | B1 | | 10/2001 | Reesby et al. |
| 6,315,718 | B1 | | 11/2001 | Sharratt |
| 6,499,158 | B1 | * | 12/2002 | Easterling .............. A61G 15/10 248/231.61 |
| 6,640,363 | B1 | | 11/2003 | Pattee et al. |
| 6,969,193 | B1 | | 11/2005 | Pigg ................. 378/180 |
| 7,152,261 | B2 | | 12/2006 | Jackson |
| 7,520,008 | B2 | | 4/2009 | Wong et al. ..................... 5/624 |
| 7,665,167 | B2 | | 2/2010 | Branch et al. ..................... 5/624 |
| 7,669,262 | B2 | | 3/2010 | Skripps et al. ..................... 5/621 |
| 7,824,353 | B2 | | 11/2010 | Matta |
| 7,832,401 | B2 | | 11/2010 | Torrie et al. ................. 128/845 |
| 7,947,006 | B2 | | 5/2011 | Torrie et al. ..................... 602/32 |
| 8,302,228 | B2 | | 11/2012 | Aboujaoude ..................... 5/648 |
| 2003/0145383 | A1 | | 8/2003 | Schwaegerle |
| 2004/0003468 | A1 | | 1/2004 | Mitsuishi et al. ................. 5/624 |
| 2004/0088793 | A1 | * | 5/2004 | Koch .................. A61G 13/101 5/621 |
| 2004/0133979 | A1 | | 7/2004 | Newkirk et al. ..................... 5/600 |
| 2004/0133983 | A1 | | 7/2004 | Newkirk et al. ..................... 5/624 |
| 2004/0148703 | A1 | | 8/2004 | Doering et al. |
| 2006/0096033 | A1 | | 5/2006 | Wong et al. |
| 2006/0117484 | A1 | * | 6/2006 | Derenne ............ A61G 13/0009 5/624 |
| 2007/0214570 | A1 | | 9/2007 | Coppens et al. |
| 2007/0251011 | A1 | | 11/2007 | Matta et al. ..................... 5/624 |
| 2007/0265635 | A1 | * | 11/2007 | Torrie ................ A61G 13/0036 606/105 |
| 2011/0184278 | A1 | | 7/2011 | Goff et al. |
| 2015/0290064 | A1 | * | 10/2015 | Kreuzer ................ A61G 13/02 128/845 |

OTHER PUBLICATIONS (Internet accessed article) St. Mark's Hospital of Salt Lake City, Utah and DePuy Orthopaedics, Inc., "*Anterior Approach Hip Replacement Surgery Yields Increased Volume and Reduced Resource Utilization*", USA, DePuy Orthopaedics, Inc., printed for IDS submission and accessed online on Dec. 12, 2014 at http://www.mizuhosi.com/wp-content/uploads/2010-AAOS-AA-Case-Study-St-Marks-Hospital.pdf.

(Internet accessed product datasheet) Mizuho Osi, "*hanaSSXT—The Ultimate Specialty Surgery Extension for Anterior Approach THA*", printed for IDS submission and accessed online on Dec. 12, 2014 at http://www.mizuhosi.com/wp-content/uploads/SSXT-COVER-8110.pdf.

(Internet accessed article), Williams, Denise, Citizen Tribune, "*Lakeway Regional receives specialized equipment to aid hip replacement surgery*", Lakeway Publishers Inc. printed for IDS submission and accessed online on Dec. 12, 2014 at http://www.mizuhosi.com/lakeway-regional-receives-specialized-equipment-to-aid-hip-replacement-surgery/.

(Internet accessed brochure) "Introducing the biggest surgical instrument in orthopedic surgery", printed for IDS submission and accessed online on Dec. 12, 2014 at http://www.becker-medical.com/img/products/pdf/4d6287cfed0a0PROfx_Print.pdf.

(Internet accessed brochure) "hanaSSXT the ultimate specialty surgery extension for anterior approach tha", printed for IDS submission and accessed online on Dec. 12, 2014 at http://2.imimg.com/data2/JK/YU/MY-2806272/speciality-surgery-extension.pdf.

Yerasimides, Jonathan G., et al., "Primary Total Hip Arthroplasty with a Minimally Invasive Anterior Approach", Seminars in Arthoplasty, 2005, pp. 186-190.

Maquet, Zubehör für Operationstische, Accessories for Operating Tables, Surgical Workplaces, Nov. 2007.

\* cited by examiner

ADAPTER FOR CONNECTING AT LEAST ONE ACCESSORY DEVICE TO AN OPERATING TABLE

CROSS REFERENCE TO RELATED APPLICATIONS

This application is a continuation pursuant to 35 U.S.C. § 120 of U.S. patent application Ser. No. 12/893,058 filed on Sep. 29, 2010, now U.S. Pat. No. 8,997,286 granted on Apr. 7, 2015, which in turn claims benefit of priority pursuant to 35 U.S.C. § 119(d) to German Patent Application No. 10 2009 047 869.8 filed on Sep. 30, 2009, all the contents of which are incorporated by reference herein.

TECHNICAL FIELD

The invention relates to an adapter for connecting at least one accessory device to an operating table.

BACKGROUND OF THE INVENTION

In the field of endoprothetics, accessory devices, e.g. plug-in devices for hip surgery are used, which are connected to a conventional operating table. For this purpose the operating table must include interfaces specifically designed for the accessory device, which allow for connecting the accessory device.

As the number of joint operations has been increasing for years, there is also an increasing number of different operating table systems, which are used in the field of endoprothetics. Against this background the invention is based on the object of creating a possibility to combine the accessory devices more flexibly than previously with different operating tables.

SUMMARY OF THE INVENTION

The invention solves this problem by an adapter for connecting at least one accessory device to an operating table, comprising a first fixing device for attaching a base body of the adapter to the operating table and a second fixing device for attaching the accessory device to the adapter, wherein the base body is formed from an X-ray transparent plate, said X-ray transparent plate including a part lying on a support surface of the operating table and another part extending beyond the support surface and forming a support surface extension for supporting a patient, when said X-ray transparent plate is attached to the operating table.

The adapter according to the invention allows for connecting an accessory device to an operating table, which does not have interfaces specifically designed for the accessory device. Furthermore the adapter itself can be used as support surface extension.

As the plate of the adapter—as support surfaces of customary operating tables if required as well—consists of an X-ray transparent material, e.g. carbon fibre reinforced plastic, the patient can be supported on the plate and be treated by means of X-ray diagnostics in the region of the plate.

Due to the part of the X-ray transparent plate lying on the support surface of the operating table, it is provided for a stable arrangement of the adapter on the operating table. Thus the above-mentioned first fixing device serving to attach the base body of the adapter to the operating table can be realized with comparatively low effort. In particular it is thus possible to connect the adapter and thus the accessory device (e.g. by means of a slide rail) in a simple manner to different operating tables.

The part of the plate forming the support surface extension is preferably arranged in a free-standing manner. This means that all parts of the adapter, in particular the above-mentioned second fixing device for attaching the accessory device to the adapter are arranged such that the area surrounding the support surface extension is kept free from said parts, which could affect the treatment by means of X-ray diagnostics of the body part supported on the support surface extension.

Preferably the part of the plate forming the support surface extension extends in the longitudinal direction of the support surface of the operating table and has a length of at least one third of the total length of the plate. Typically the length is at least 400 mm. Thus it is guaranteed that the adapter provides a sufficiently large additional patient support surface, which can be used for supporting the patient according to requirements in different positions (in particular in pelvis free position).

In a preferred embodiment the plate can be pushed from one end of the support surface in the longitudinal direction onto the support surface until a first limit stop arranged at the adapter comes to bear against a second limit stop arranged at the operating table and said one part of the plate lies on the support surface. Preferably the part of the plate lying on the support surface has substantially the same width as the support surface. The above-mentioned part of the plate and the support surface of the operating table thus form an overlapping arrangement, the longitudinal sides of which are aligned with each other. Depending on the application, the plate can however also be smaller than the support surface of the operating table.

In a further advantageous embodiment the first fixing device comprises a rail arranged at the plate and a hold-down device, which can be fixed to the operating table, said hold-down device including a locking element insertable into the rail, which locking element can be locked in the rail. The rail is e.g. formed as elongated recess in the top surface of the plate or as separate component attached to the plate and preferably arranged at said end of the plate, which is pushed onto the support surface of the operating table. Thereby the recess and the locking element inserted therein are to be sized preferably such that the top surface of the locking element is formed flush with the top surface of the plate.

In a preferred embodiment the hold-down device can be moved along a guide, which is mounted laterally on the operating table at the longitudinal direction thereof. Said guide is e.g. formed as slide rail, on which the hold-down device can be moved when the plate is pushed onto the support surface.

Preferably the first fixing device serving to attach the base body of the adapter to the operating table comprises a handle screw having a contact surface, which can be screwed on the bottom surface of the operating table for securing the plate. Thereby the adapter is secured to the operating table from the bottom surface.

An X-ray transparent cushion can be attached to the top surface of the plate of the adapter. This cushion preferably has a multilayered structure, wherein an EPDM backing layer is superimposed by viscoelastic foam. Attaching the cushion is e.g. carried out by means of a velcro fastener in the form of loop and adhesive tapes, which are attached to the bottom surface of the cushion or on the top surface of the plate of the adapter.

Preferably the above-mentioned second fixing device, by means of which the accessory device is attached to the adapter, comprises a shaft receptacle, in which a plug-in shaft of the accessory device is pluggable.

In a particularly preferred embodiment the shaft receptacle is attached to a carriage, which can be moved along a guide shaft. Thereby it is possible to move the shaft receptacle together with the plug-in shaft of the accessory device inserted therein to adjust e.g. the accessory device to the proportions of the patient and then fix it on the guide shaft.

Preferably the adapter is designed for connecting a plug-in device for hip endoprothetics. However it is also possible to use the adapter for other accessory devices, which are to be attached to an operating table.

According to a further aspect of the invention a system is provided, comprising an operating table, at least one accessory device as well as an adapter of the above-mentioned type.

BRIEF DESCRIPTION OF THE DRAWINGS

The invention will be explained in the following on the basis of the Figures, wherein.

DETAILED DESCRIPTION OF THE EMBODIMENTS

Figure 3:
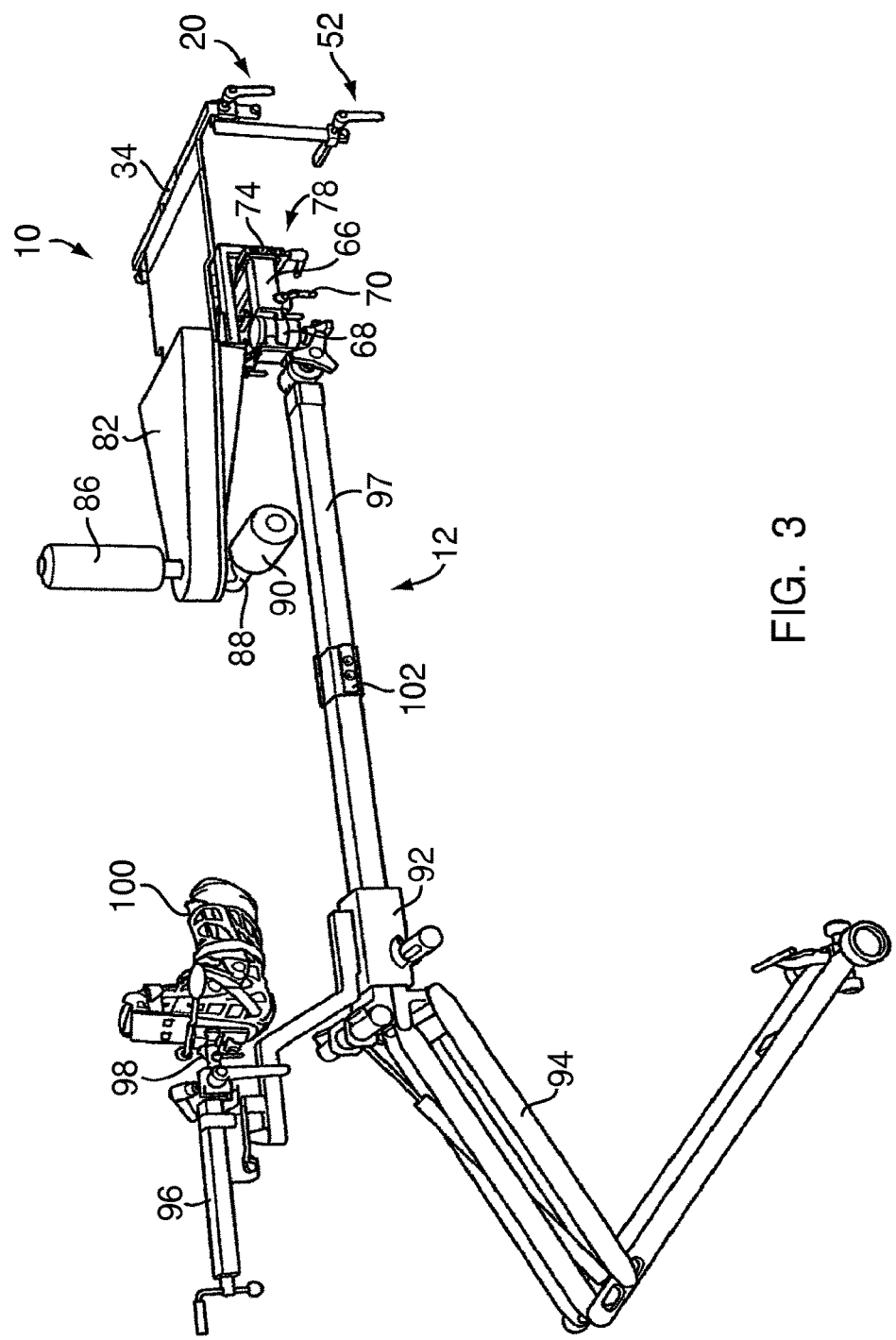
FIG. 3 shows the adapter with mounted plug-in device.

The embodiment described in the following is directed to an adapter, generally referred to with 10, serving to connect an accessory or plug-in device 12 for hip surgery to an operating table 14. The plug-in device 12 mounted on the adapter 10 is illustrated in FIG. 3. A part of the operating table 14 can e.g. be seen in FIG. 4.

On the basis of FIGS. 1 and 2 in the following first an overview of the elements forming the adapter 10 is provided.

Figure 1:
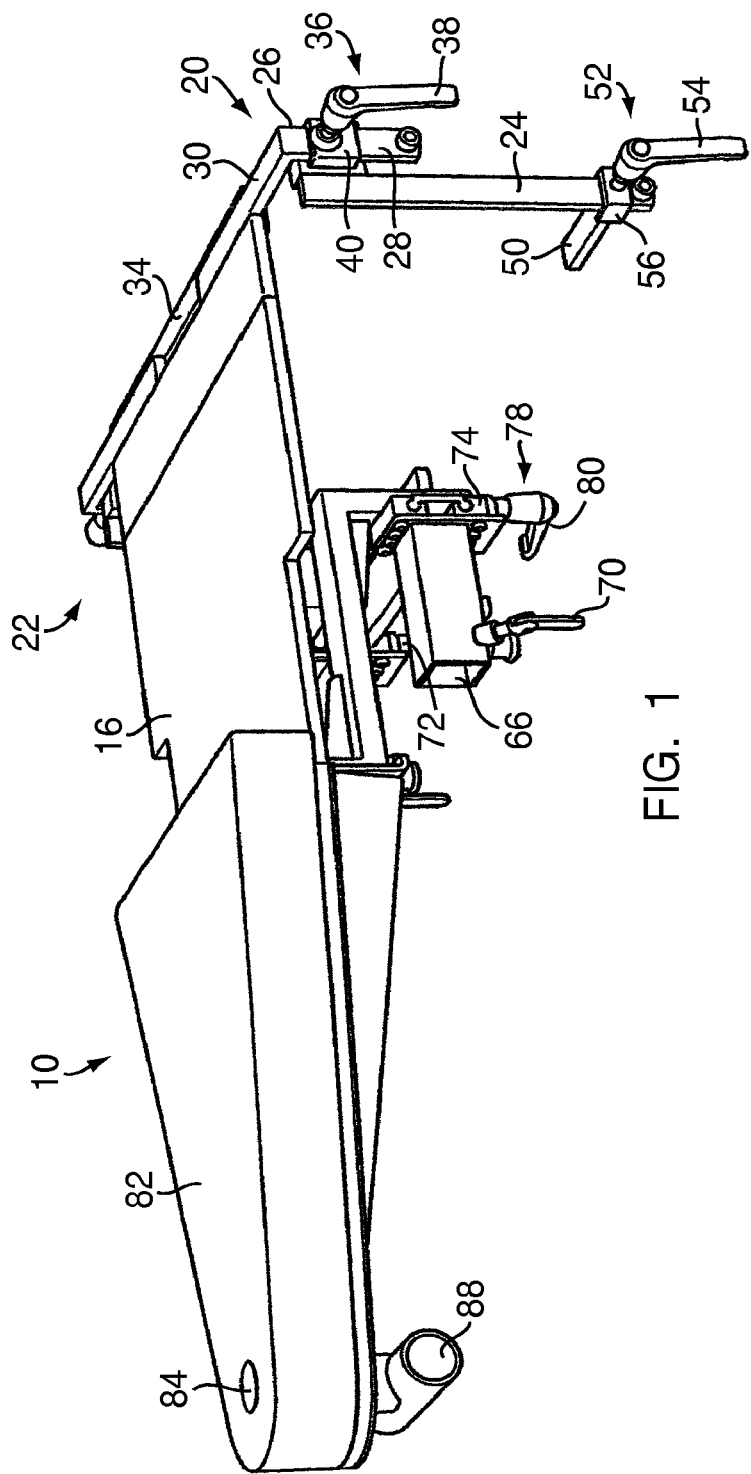
FIG. 1 shows a perspective view of an adapter according to the invention.
Figure 2:
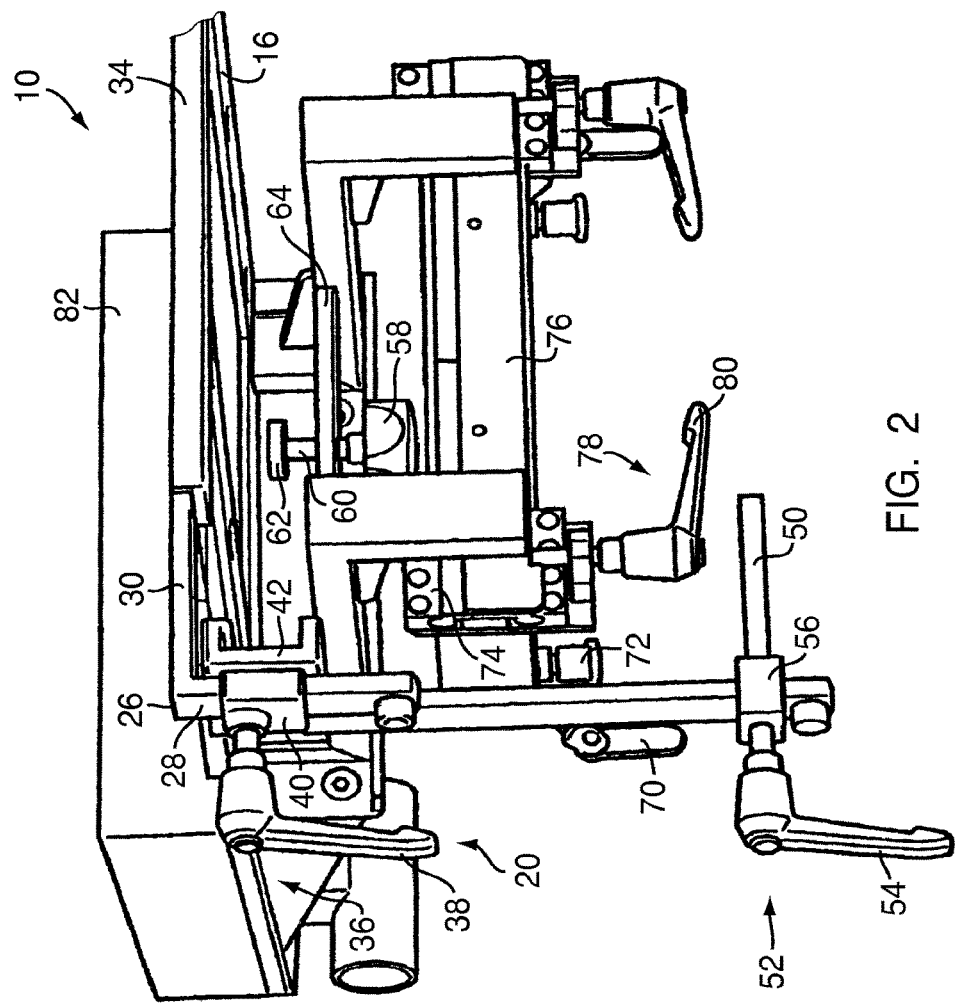
FIG. 2 shows a further perspective view of the adapter.

As shown in FIGS. 1 and 2, the base body of the adapter 10 is formed from a plate 16 consisting of a carbon fibre reinforced plastic. This plastic is X-ray transparent.

The adapter 10 further comprises two hold-down devices 20, 22 serving to fix the adapter 10 to the two longitudinal sides of the operating table 14. Of the two hold-down devices 20, 22, which are substantially identical in construction and function, in FIGS. 1 and 2 only the device referred to with 20 is shown in detail and described in the following.

The hold-down device 20 includes a straight guide rod 24 being arranged perpendicular to the plate 16 in the mounted condition and an L-shaped rod 26. In the mounted condition the short leg 28 is arranged perpendicular and the long leg 30 is arranged parallel to the plate 16.

The long leg 30 of the L-shaped rod 26 is inserted into a guide rail 34 in the mounted condition, which is attached to one end of the plate 16 in the lateral direction.

In order to arrest the long leg 30 of the L-shaped rod 26 in the guide rail 34, a locking device, generally referred to with 36, is provided. The locking device 36 comprises a lever screw 38, a receptacle 40 and a slide rail block 42 having a C-section. The slide rail block 42 can be attached to a slide rail 44, which is mounted on the longitudinal side of the operating table 14 (cf. FIG. 5). The short leg 28 of the L-shaped rod 26 is movably guided through the receptacle 40. The lever screw 36 is screwed into the receptacle 40 with its threaded shank, being not illustrated in detail. By turning the lever screw 38 the threaded shank can be brought into contact with the short leg 28 of the L-shaped rod 26. The short leg 28 can thus be locked in a desired height in the receptacle 40.

The hold-down device 20 further comprises a further straight rod 50, which is movably arranged at the guide rod 24. The rod 50 is arrestable by means of a locking device 52 on the guide rod 24. The locking device 52 is formed from a lever screw 54 and a receptacle 56. The lever screw 54 is screwed into the receptacle 56 with its threaded shank, being not illustrated in detail. By turning the lever screw 54 the threaded shank can be screwed into the receptacle 56 until the threaded shank 56 comes into contact with the guide rod 24, whereby the rod 50 is locked in the desired height on the guide rod 24.

As shown in FIG. 2, the adapter 10 further includes a handle screw 58 having a threaded shank 60, on the end, being the upper end in FIG. 2, of which a contact surface 62 is attached. The threaded shank 60 is screwed through a threaded bore, being not illustrated in detail, which is formed in a frame part 64 of the adapter 10. By turning the lever screw 58 the contact surface 62 can be brought into contact with the bottom surface of the support surface 15 to additionally secure the plate 16.

For attaching the plug-in device 12, shown in FIG. 3, the adapter 10 includes a shaft receptacle 66, in which a plug-in interface 68 (cf. FIG. 10) of the plug-in device 12 can be inserted. The plug-in interface 68 inserted into the shaft receptacle 66 is arrestable by means of a spring-loaded safety bolt 72. On the shaft receptacle 66 a tommy screw 70 is additionally provided serving to eliminate the play of the plug-in interface 68 inserted into the plug-in receptacle 66.

The shaft receptacle 66 is attached to a frame-shaped carriage 74. The carriage 74 is guided movably on a guide shaft 76 extending in the lateral direction in parallel to the plate 16, as can best be seen in FIG. 2.

The carriage 74 can be locked to the guide shaft 76 by means of a locking device 78. The locking device 78 comprises a lever screw 80, which is screwed into the carriage 74 with its threaded shank, being not illustrated in detail. If the lever screw 80 is turned until the threaded shank comes into contact with the guide shaft 76, the carriage 74 is locked on the guide shaft 76. By loosening the lever screw 80 the carriage 74 together with the shaft receptacle 66 and the plug-in interface 68 of the plug-in device 12 being seated in the shaft receptacle 66 can be moved along the guide shaft 76.

As shown in FIG. 1, an X-ray transparent cushion 82 is attached to the top surface of the plate 16. The cushion 82 includes a through hole 84, into which an end of the countertraction post 86 can be inserted. The countertraction post 86 is covered in a cushion 87 (cf. FIG. 12). On the plate 16 a post receptacle 85, not shown in the Figures, is provided for the countertraction post 86, which is oriented toward the hole 84 of the cushion 82 (cf. FIG. 9). Further an abutment receptacle 88 for attaching an abutment 90 (cf. FIG. 13) is formed on the plate 16.

In the following it will be shortly explained on the basis of FIGS. 4 to 13 how the plug-in device 12 is connected to the operating table 14 by means of the adapter 10.

Figure 4:
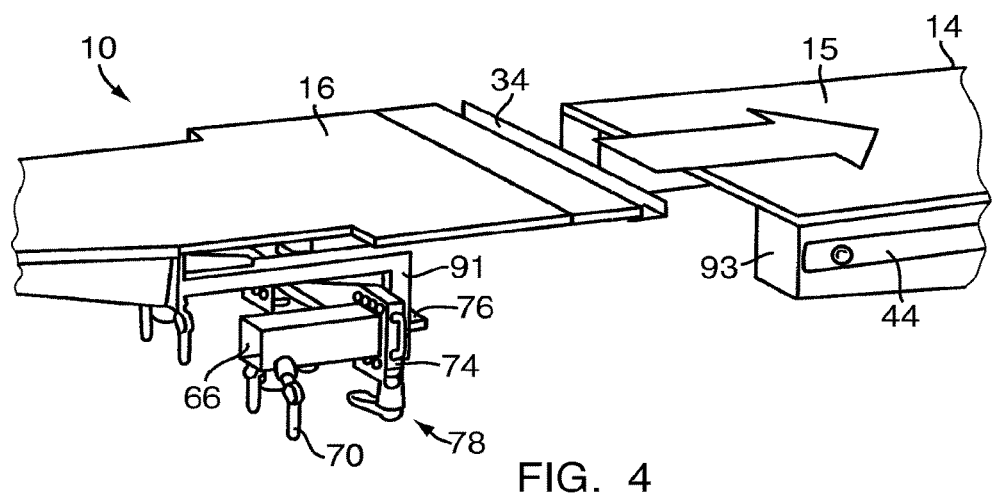
FIG. 4 shows an illustration of how the plate is pushed onto the support surface of the operating table.

As indicated by the arrow in FIG. 4, first the plate 16 is pushed onto a support surface 15 of the operating table 14. The support surface 15 is typically a hard paper plate, on which a cushion, not being shown, is later applied. In the mounted condition the plate 16 is thus arranged between the support surface 15 and said cushion.

In FIG. 4 the plate 16 is pushed onto the support surface 15 to the right to such an extent that a first limit stop arranged at the adapter 10 comes to bear against a second limit stop arranged at the operating table 14. In the present embodiment a frame part may form the above-mentioned first limit stop, while the second limit stop is constituted by a front end face 93 of the operating table 14. To assure a precise positioning of the adapter 10 on the support surface 15, one or more marking lines can be provided on the plate 16, which are aligned with the edges of the support surface 15 in case of correct positioning.

Figure 5:
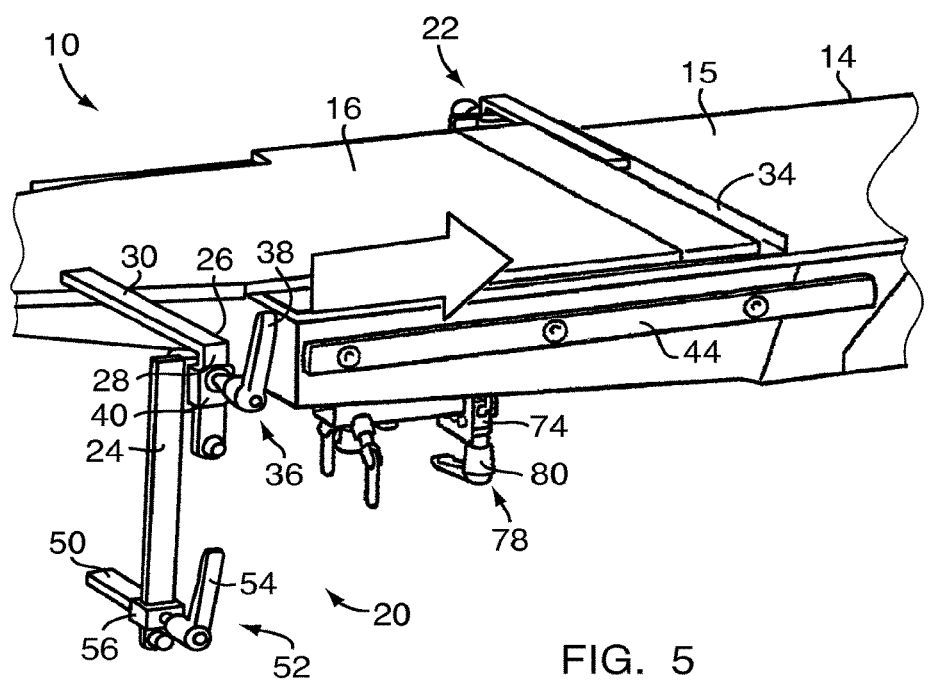
FIG. 5 shows an illustration of how the hold-down device is attached to the operating table.
Figure 6:
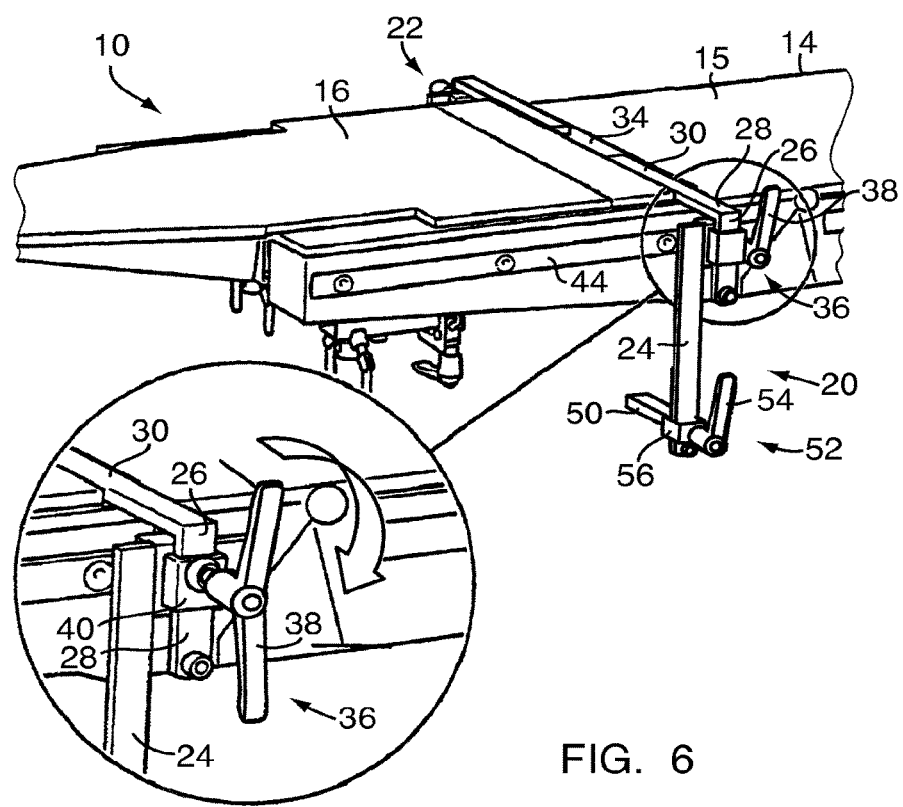
FIG. 6 shows an illustration of how the plate is fixed on the operating table by means of the hold-down device.

As shown in FIG. 5, subsequently the hold-down device 20 is pushed onto or put in from the side to the slide rail 44 attached to the operating table 14. The long leg 30 of the L-shaped rod 26 is then inserted into the guide rail 34, as shown in FIG. 6. Subsequently, as indicated by the arrow in the enlarged partial view according to FIG. 6, the lever screw 38 is tightened manually, to arrest the long leg 30 of the L-shaped rod 26 in the guide rail 34. The same is done with the other hold-down device 22.

Figure 7:
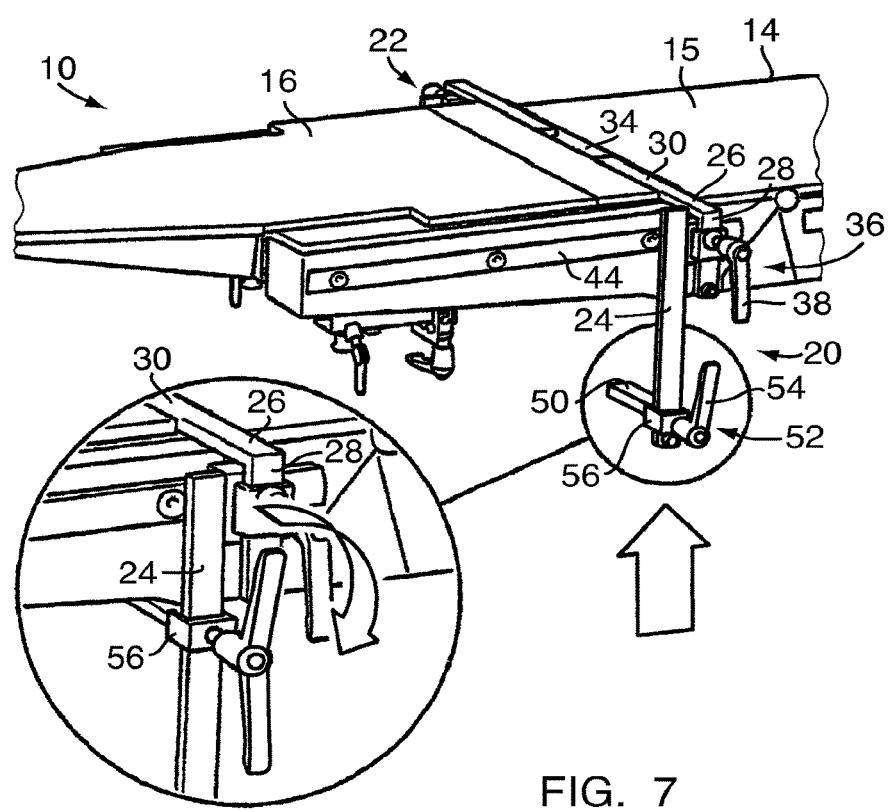
FIG. 7 shows an illustration of how the plate fixed to the operating table is secured from below.

As illustrated in FIG. 7, the rod 50 is then moved upwards along the guide rod 24 until it abuts from below against the operating table 14, e.g. against the shaft structure thereof. By tightening the lever screw 54 the rod 50 is locked on the operating table 14.

Figure 8:
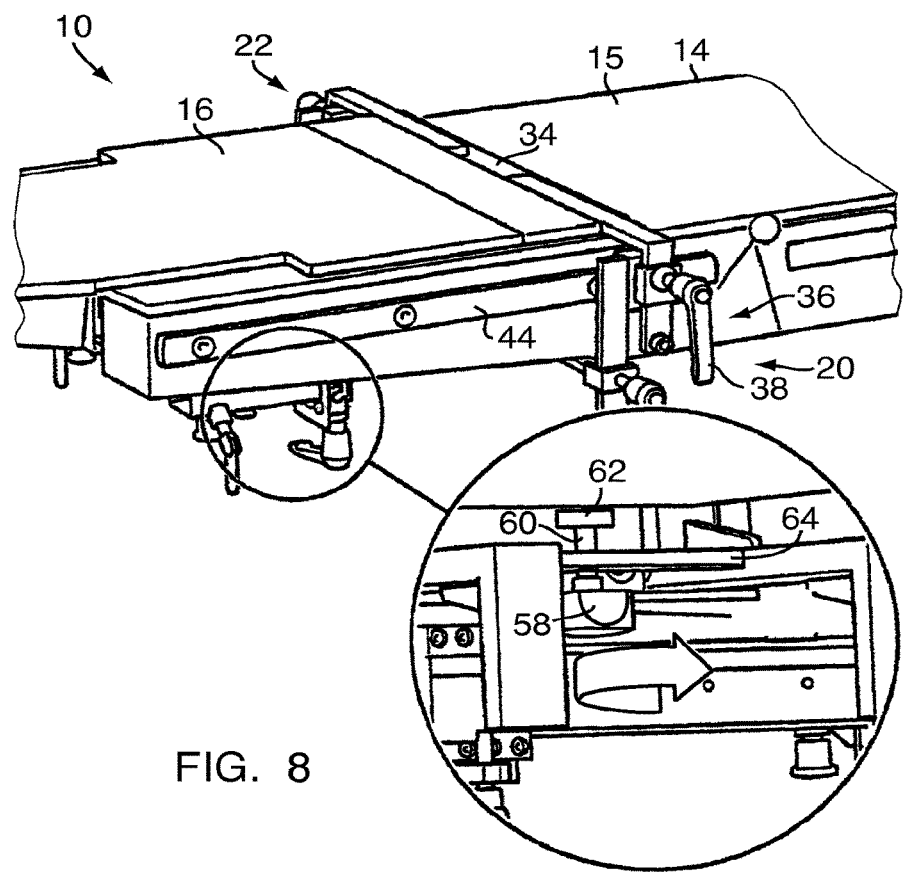
FIG. 8 shows an illustration of how the plate attached to the operating table is additionally secured from below.

As shown in FIG. 8, subsequently the handle screw 58 is tightened to bring the contact surface 62 into contact with the bottom surface of the support surface 15. If the contact surface 62 abuts against the bottom surface of the plate 16, the adapter 10 is additionally secured to the operating table 14.

Figure 9:
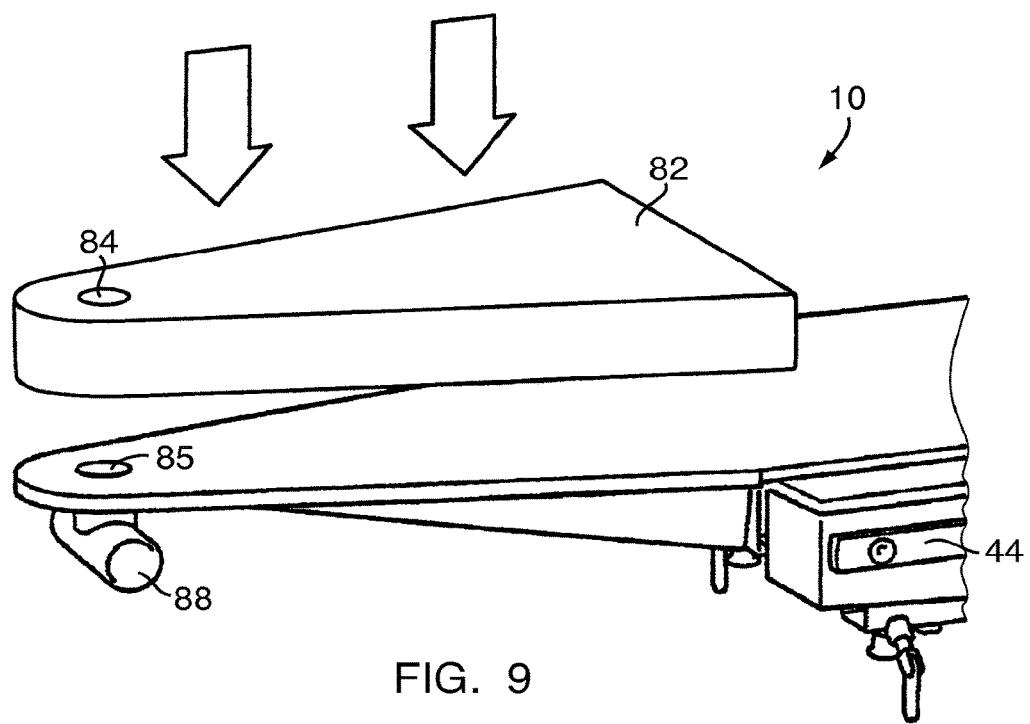
FIG. 9 shows an illustration of how a cushion is attached to the plate.

Subsequently the cushion 82 is laid on the plate 16 and is fixed thereon by means of loop tapes and adhesive tapes, not being shown, which are arranged at the bottom surface of the cushion 82 or the upper surface of the plate 16, as shown in FIG. 9.

Figure 10:
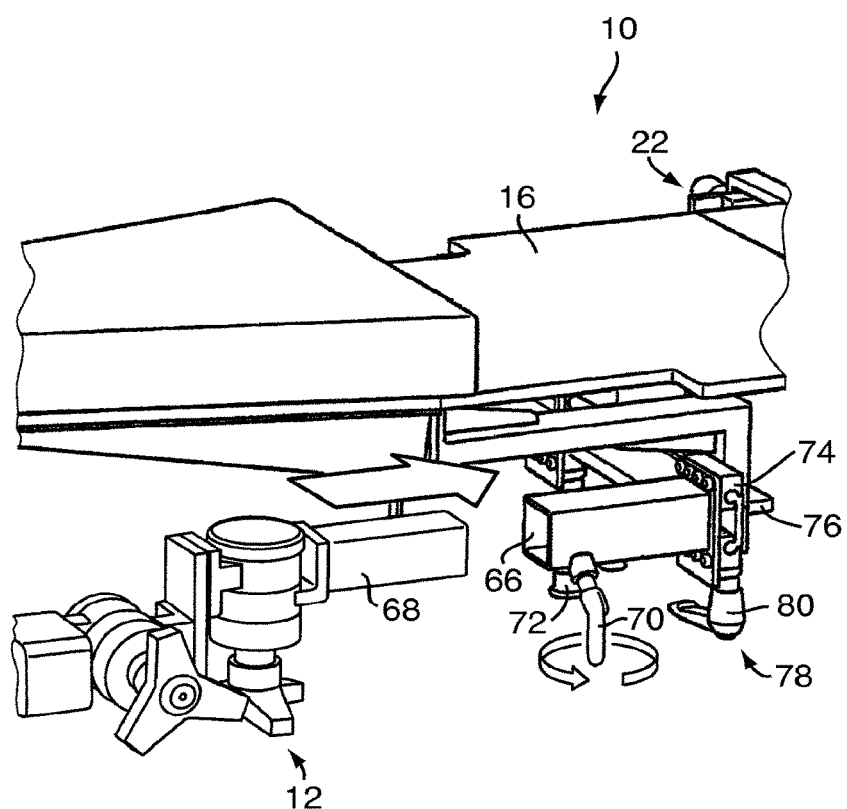
FIG. 10 shows an illustration of how an accessory device is attached to the adapter.

After the adapter 10 has now been completely mounted to the operating table 14, the plug-in device 12 can be connected to the adapter 10. This is shown in FIG. 10. For this, the plug-in interface 68 of the plug-in device 12 is inserted into the shaft receptacle 66 of the adapter 10. If the plug-in interface 68 is secured by means of the spring-loaded safety bolt 72 in the shaft receptacle 68, the lever screw 70 is tightened to eliminate the play.

Figure 11:
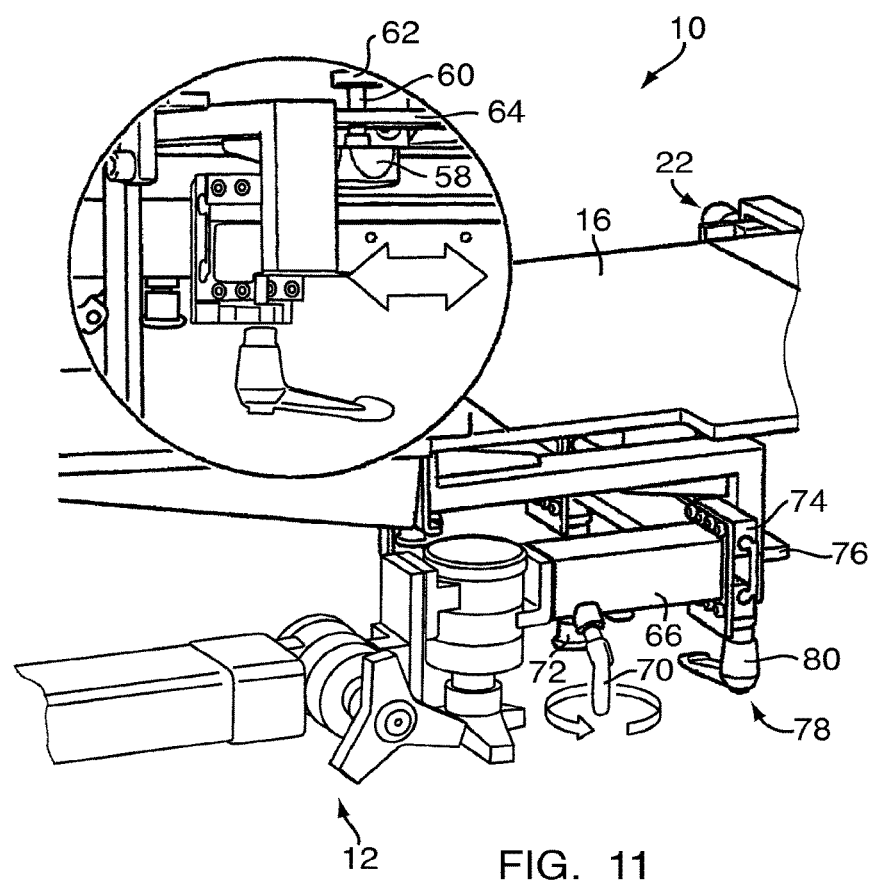
FIG. 11 shows an illustration of how a carriage provided on the adapter is moved.

In FIG. 11 it is shown how the carriage 74, on which the shaft receptacle 66 is attached, can be moved along the guide shaft 76 to position the plug-in device 12 correctly on the operating table 14. For this, first the lever screw 80 has to be loosened, whereby the carriage 74 is freely movable on the guide shaft 76. If the carriage 74 is brought into the desired position on the guide shaft 76, the lever screw 80 is tightened again, to arrest the carriage 74 on the guide shaft 76.

Figure 12:
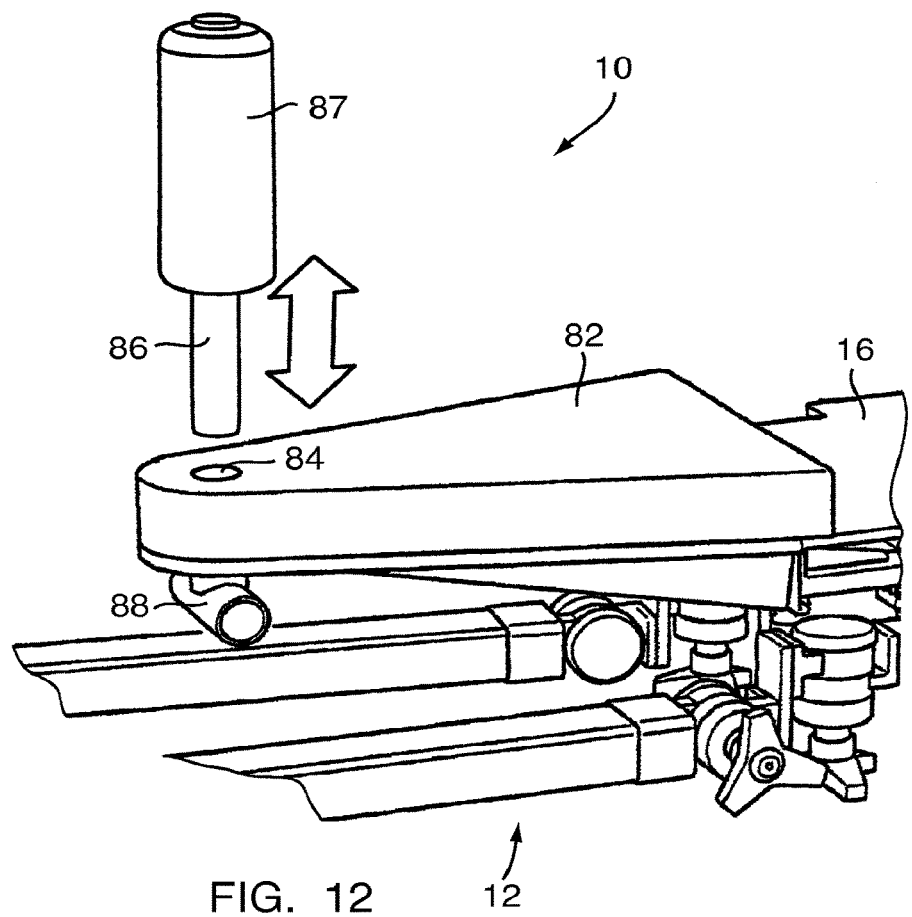
FIG. 12 shows an illustration of how a countertraction post is attached to the adapter.

If the cushion 82 is attached to the plate 16, the countertraction post 86 can, as shown in FIG. 12, be inserted into the hole 84 formed in the cushion 82 and be fixed in the abutment receptacle 85 (cf. FIG. 9), which is formed in the plate 16.

Figure 13:
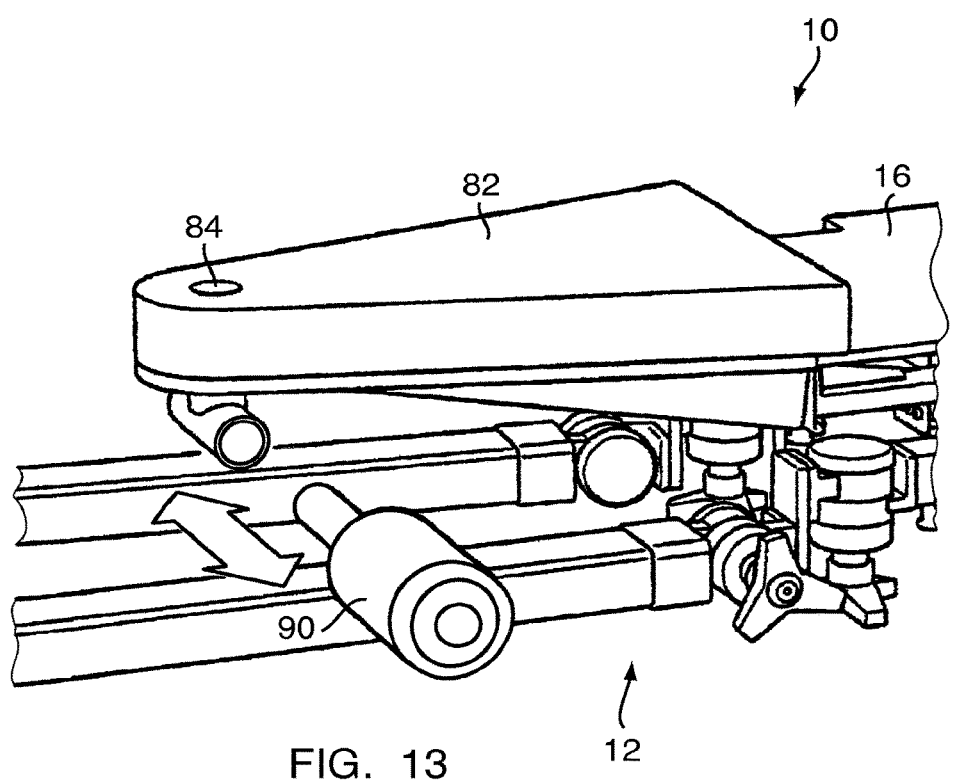
FIG. 13 shows an illustration of how an abutment is attached to the adapter.

FIG. 13 finally shows, how the abutment 90 is plugged in the abutment receptacle 88 positioned on the bottom surface of the plate 16.

For the sake of completeness, in FIG. 3 the plug-in device 12 being used for hip surgery, as mentioned above, is shown together with the adapter 10, on which it is mounted. The plug-in device 12, known per se, comprises a plug-in shaft 91 with the plug-in interface 68, a shaft carriage 92, a support foot 94, a spindle traction mechanism 96, a rotary tilting device 98 as well as an extension shoe 100. A slide rail bolt 102 for attaching further accessories, e.g. femur hooks, leg holders etc. is provided on the plug-in shaft 91.

As becomes also apparent from FIG. 3 said part of the plate 16, to which the cushion 82 is attached and which does not lie on the support surface 15 of the operating table 14, forms a fully functional support surface extension of the operating table 14 in the longitudinal direction thereof. However, the invention is not limited to such an embodiment. Thus, the adapter 10 can also be formed such that it forms exclusively or additionally a support surface extension of the operating table 14 in the lateral direction.

In the present embodiment two plug-in devices of the described type can be connected on both sides of the adapter 10 and thus on both sides of the operating table 14. However, the invention is neither limited to the number of mountable plug-in devices nor to the type thereof.

What is claimed is:

1. An operating table adapter, comprising: a table mount configured to removably attach the adapter to an operating table; and an accessory mount configured to attach a surgery extension device to the adapter; wherein the adapter includes a free-standing, X-ray transparent member; wherein the X-ray transparent member includes a first part comprising a lower surface configured to directly contact an upper support surface of the operating table, and a second part configured to extend beyond the upper support surface in a longitudinal direction of the upper support surface when the adapter is mounted to the operating table via the table mount; wherein the second part of the X-ray transparent member comprises a support surface extension configured to support a patient when the adapter is attached to the operating table; and the table mount comprising: a guide rod, the guide rod being elongated and extending downward with respect to the X-ray transparent member when the adapter is attached to the operating table; and an abutment element, the abutment element being movable vertically along the guide rod towards and away from the X-ray transparent member, and being lockable along the guide rod; wherein when the operating table adapter is positioned on said operating table, the abutment element is movable along the guide rod and lockable against a bottom surface of the operating table, to thereby grasp the operating table between the first part of the X-ray transparent member and the abutment element.

2. The operating table adapter of claim 1:
   comprising a second guide rod, the second guide rod being elongated and extending downward with respect to the X-ray transparent member; and a second abutment element, the second abutment element being movable vertically along the second guide rod towards and away from the X-ray transparent member, and being lockable in a plurality of positions along the second guide rod.

3. The operating table adapter of claim 1, wherein the table mount includes a slide rail block attachable to a slide rail disposed on a longitudinal side of the operating table.

4. The operating table adapter of claim 1,
wherein the abutment element comprises a rod; and
further comprising a lever screw adapted for locking the abutment element with respect to the guide rod.

5. The operating table adapter of claim 1,
further comprising a hip surgery extension device removably attached to the adapter, the hip surgery extension device comprising a pivotable elongated arm, and a boot for holding a foot.

6. The operating table adapter of claim 1, wherein the X-ray transparent member is a plate made of a carbon fiber reinforced plastic material.

7. The operating table adapter of claim 1, the table mount further comprising:
two L-shaped rods, the L-shaped rods each comprising a horizontal leg and a vertical leg;
a guide rail connected to the X-ray transparent member; the guide rail being shaped for receiving the respective horizontal legs of the two L-shaped rods;
wherein the horizontal legs of the L-shaped rods are positioned in the guide rail when the operating table adapter is positioned on said operating table;
further comprising a second guide rod, and a second abutment element vertically movable along the second guide rod;
wherein the guide rod and the second guide rod are each connected to a respective vertical leg of one of said L-shaped rods.

8. An operating table extension system, comprising: an adapter; a table mount configured to removably attach the adapter to an operating table; and an accessory mount configured to removably attach an accessory device to the adapter, the accessory mount including a shaft receptacle disposed on the adapter configured to receive a plug-in shaft of an accessory device, when present; wherein the adapter includes an X-ray transparent elongated member having a first part configured to a rest on top of the operating table, and a second part configured to extend beyond the support surface in a longitudinal direction of the support surface when the adapter is mounted to the operating table via the table mount; wherein the second part of the X-ray transparent elongated member comprises a support surface extension configured to support a patient when the adapter is attached to the operating table; the table mount further comprising: an L-shaped rod, the L-shaped rod comprising a horizontal leg and a vertical leg; a guide rail connected to the X-ray transparent member; the guide rail being shaped for receiving the horizontal leg of the L-shaped rod; wherein the horizontal leg of the L-shaped rod is positioned in the guide rail when the operating table adapter is positioned on said operating table; and at least one abutment element, the at least one abutment being movable and lockable against a bottom of the operating table, when present, for holding the adapter on the operating table.

9. The operating table extension system of claim 8, wherein the table mount includes a member that is attachable to a slide rail disposed on a longitudinal side of the operating table.

10. The operating table extension system of claim 8: the table mount further comprising a second L-shaped rod, the second L-shaped rod comprising a horizontal leg and a vertical leg; wherein the guide rail comprises a channel; wherein the respective horizontal legs of the L-shaped rod and the second L-shaped rod are both positioned in the channel of the guide rail when the operating table adapter is positioned on said operating table; wherein the L-shaped rod and second L-shaped rod are both part of a hold down device for holding the operating table extension system on said operating table when present.

11. The operating table extension system of claim 8, wherein the X-ray transparent elongated member is a carbon fiber reinforced plastic plate.

12. The operating table extension system of claim 8 further comprising: a guide rod connected to the vertical leg of the L-shaped rod; and the abutment element being slideable along the guide rod and lockable in place along the guide rod; wherein when the operating table extension system is positioned on said operating table, the abutment element is movable and lockable against a surface of the operating table, to thereby grasp the operating table between the first part of the X-ray transparent member and the abutment element.

13. An operating table extension system, comprising: an adapter that includes: a plate; a table mount configured to attach the adapter to an operating table; and an accessory mount configured to receive a surgery extension device, when present, to connect the surgery extension device to the adapter; wherein the plate includes a first part configured to contact an upper support surface of the operating table and a second part configured to extend beyond the upper support surface in a longitudinal direction of the upper support surface when the adapter is mounted to the operating table via the table mount; the table mount comprising: an L-shaped rod, the L-shaped rod comprising a horizontal leg and a vertical leg; and a guide rail, the guide rail being shaped for holding the horizontal leg of the L-shaped rod; wherein the horizontal leg of the L-shaped rod is positioned in the guide rail when the operating table adapter is positioned on said operating table; and at least one abutment element, the at least one abutment being movable and lockable against the operating table, when present, for holding the adapter on the operating table.

14. The operating table extension system of claim 13: the table mount further comprising: a guide rod connected to the vertical leg of the L-shaped rod; and the abutment element being slideable along the guide rod and lockable in place along the guide rod; wherein when the operating table extension system is positioned on said operating table, the abutment element is movable and lockable against a surface of the operating table, to thereby grasp the operating table between the plate and the abutment element.

15. The operating table extension system of claim 13, wherein the table mount further comprises a member configured to attach to a rail disposed on a longitudinal side of the operating table, when present.

16. The operating table extension system of claim 13: wherein the operating table extension system is configured for use in hip surgeries; the surgery extension device configured to attach to the accessory mount, the surgery extension device comprising a boot for holding a foot of a patient.

17. The operating table extension system of claim 13, wherein the plate is an X-ray transparent plate; and
wherein the guide rail comprises an elongated horizontal channel shaped for receiving the horizontal leg of the L-shaped rod.

18. The operating table extension system of claim 13:
the table mount further comprising:
a second L-shaped rod, the second L-shaped rod comprising a horizontal leg and a vertical leg;
   wherein the respective horizontal legs of the L-shaped rod and the second L-shaped rod are both positioned in the guide rail when the operating table adapter is positioned on said operating table; and
two guide rods, each guide rod movably connected to a vertical leg of the L-shaped rod, each guide rod being vertically movable with respect to the respective vertical leg of the L-shaped rod; and
two abutment elements, each abutment element being slideable along a respective one of said two guide rods and being lockable in place along the respective guide rod;
wherein when the operating table extension system is positioned on said operating table, the two abutment elements are each movable and lockable against a surface of the operating table, to thereby grasp the operating table between the plate and the two abutment elements.

19. The operating table adapter of claim 13: wherein the surgery extension device comprises: a hip surgery extension device removably attached to the adapter, the hip surgery extension device comprising a pivotable elongated arm, and a boot for holding a foot; and a counteraction post extending up from the plate, positioned for limiting movement of a patient, when present, towards the boot.

\* \* \* \* \*